(12) United States Patent
Falardeau et al.

(10) Patent No.: US 10,980,645 B2
(45) Date of Patent: Apr. 20, 2021

(54) INSTRUMENT NAVIGATION IN COMPUTER-ASSISTED HIP SURGERY

(71) Applicant: ORTHOSOFT, INC., Montreal (CA)

(72) Inventors: Bruno Falardeau, Verdun (CA); Myriam Valin, Laval (CA); Benoit Pelletier, Montreal (CA); Francois Paradis, Boucherville (CA)

(73) Assignee: ORTHOSOFT ULC, Montreal (CA)

( * ) Notice: Subject to any disclaimer, the term of this patent is extended or adjusted under 35 U.S.C. 154(b) by 961 days.

(21) Appl. No.: 14/934,894

(22) Filed: Nov. 6, 2015

(65) Prior Publication Data

US 2016/0135900 A1    May 19, 2016

Related U.S. Application Data

(60) Provisional application No. 62/076,123, filed on Nov. 6, 2014.

(51) Int. Cl.
*A61F 2/46* (2006.01)
*A61B 34/20* (2016.01)
(Continued)

(52) U.S. Cl.
CPC ............ *A61F 2/4609* (2013.01); *A61B 34/20* (2016.02); *A61B 17/1666* (2013.01);
(Continued)

(58) Field of Classification Search
CPC ............ A61B 17/1664; A61B 17/1666; A61B 17/1742; A61B 17/1746; A61B 17/175;
(Continued)

(56) References Cited

U.S. PATENT DOCUMENTS

| 8,165,366 B2 * | 4/2012 | Haimerl | A61B 90/36 |
| | | | 382/128 |
| 2006/0100504 A1 * | 5/2006 | Jansen | A61B 5/064 |
| | | | 600/424 |

(Continued)

FOREIGN PATENT DOCUMENTS

WO    2013130326 A1    9/2013

*Primary Examiner* — Marcela I. Shirsat
(74) *Attorney, Agent, or Firm* — Norton Rose Fulbright Canada LLP (57) ABSTRACT

A computer-assisted surgery system comprises a calibrating instrument adapted to be applied to a pelvis in a known manner, and a surgical instrument. A computer-assisted processor unit operating a surgical assistance procedure and comprises at least one portable inertial sensor unit configured to be connected to the at least one calibrating instrument and the at least one surgical instrument, the portable inertial sensor unit outputting readings representative of its orientation. A geometrical relation data module provides a geometrical relation data between the orientation of the portable inertial sensor unit, of the calibrating instrument and of the surgical instrument. A coordinate system module sets a coordinate system of the pelvis in which an anterior-posterior axis of the pelvis is generally in a direction of gravity, and in which a medio-lateral axis of the pelvis is obtained from readings of the at least one portable inertial sensor unit on the calibrating instrument using the geometrical relation data therebetween. A tracking module tracks movements of the at least one surgical instrument relative to the coordinate system using readings from the inertial sensor unit on the surgical instrument using the geometrical relation data therebetween, and calculates navigation data for the movements, the navigation data relating the orientation of the surgical instrument to the orientation of the pelvis. An interface outputs the navigation data.

11 Claims, 3 Drawing Sheets

(51) Int. Cl.
*A61B 17/16* (2006.01)
*A61B 90/00* (2016.01)

(52) U.S. Cl.
CPC . *A61B 2034/2048* (2016.02); *A61B 2090/363* (2016.02); *A61B 2560/0223* (2013.01); *A61B 2560/0487* (2013.01)

(58) Field of Classification Search
CPC . A61B 34/20; A61B 34/25; A61B 2034/2046; A61B 2034/2048; A61B 2034/2068; A61B 2034/2074; A61B 2034/252; A61B 2034/254; A61B 2560/0223; A61B 2560/0487; A61B 2090/363; A61B 5/064; A61F 2/4609; A61F 2002/4681
USPC .......................................... 600/424; 606/130
See application file for complete search history.

(56) References Cited

U.S. PATENT DOCUMENTS

| | | | |
|---|---|---|---|
| 2010/0076505 A1 | 3/2010 | Borja | |
| 2011/0275957 A1 | 11/2011 | Bhandari | |
| 2012/0157887 A1 | 6/2012 | Fanson et al. | |
| 2012/0277634 A1* | 11/2012 | Proulx | G01C 25/005 600/595 |
| 2014/0031829 A1* | 1/2014 | Paradis | A61B 34/20 606/102 |
| 2014/0052149 A1* | 2/2014 | van der Walt | A61F 2/4657 606/130 |
| 2014/0135658 A1* | 5/2014 | Hladio | A61F 2/4609 600/595 |

* cited by examiner

INSTRUMENT NAVIGATION IN COMPUTER-ASSISTED HIP SURGERY

CROSS-REFERENCE TO RELATED APPLICATION

The present application claims priority on U.S. Provisional Patent Application No. 62/076,123, filed on Nov. 6, 2014, and incorporated herein by reference.

TECHNICAL FIELD

The present application relates to computer-assisted surgery using inertial sensors and more particularly to acetabular cup positioning procedure in hip surgery.

BACKGROUND OF THE ART

In hip arthroplasty, the acetabulum is reamed to subsequently receive therein an acetabular cup. The acetabular cup is an implant that is received in the reamed acetabulum and serves as a receptacle for a femoral head or femoral head implant. Accordingly, tools such as a reamer and a cup impactor are used in the procedure. One of the challenges in such procedures is to provide an adequate orientation to the acetabular cup. Indeed, an inaccurate orientation may result in a loss of movements, improper gait, and/or premature wear of implant components. For example, the acetabular cup is typically positioned in the reamed acetabulum by way of an impactor. The impactor has a stem at an end of which is the acetabular cup. The stem is handled by an operator that impacts the free end so as to drive the acetabular cup into the acetabulum. It may however be important that the operator holds the stem of the impactor in a precise three-dimensional orientation relative to the pelvis so as to ensure the adequate orientation of the acetabular cup, in terms of inclination and anteversion.

For this purpose, computer-assisted surgery has been used in hip surgery in order to help the operator in positioning and orienting the reamer and the impactor to a desired orientation. Among the various tracking technologies used in computer-assisted surgery, optical navigation, C-arm validation and manual reference guides have been used. The optical navigation requires the use of a navigation system, which adds operative time. It also requires pinning a reference on the patient, which adds to the invasiveness of the procedure. Moreover, it is bound to line-of-sight constraints which hamper the normal surgical flow. C-arm validation requires the use of bulky equipment and the validation is not cost effective. Moreover, it does not provide a quantitative assessment of the cup positioning once done, and is generally used post-operatively as opposed to intra-operatively. Finally, manual jigs, such as an A-frame, do not account for the position of the patient on the operative table.

Accordingly, inertial sensors are used for their cost effectiveness and the valuable information they provide.

SUMMARY

Therefore, in accordance with an embodiment of the present disclosure, there is provided a method for navigating a surgical instrument relative to a pelvis in computer-assisted hip surgery comprising: with a patient in a supine position on a table plane: creating a coordinate system for a pelvis with an inertial sensor unit, the coordinate system using a direction of gravity for setting an anterior-posterior axis of the pelvis, and comprising a medio-lateral axis of the pelvis; tracking the inertial sensor unit coordinate system of the pelvis; setting an orientation of at least one surgical instrument with an inertial sensor unit thereon by determining three rotational degrees of freedom of the instrument in the coordinate system of the pelvis; tracking movements of the at least one surgical instrument relative to the coordinate system using readings from the inertial sensor unit on the surgical instrument; and outputting navigation data for the movements, the navigation data relating the orientation of the surgical instrument to the orientation of the pelvis.

Further in accordance with the embodiment of the present disclosure, outputting navigation data comprises outputting anteversion and/or inclination angles of the surgical instrument relative to the pelvis.

Still further in accordance with the embodiment of the present disclosure, creating the coordinate system for the pelvis comprises obtaining the medio-lateral axis from an instrument supporting the inertial sensor unit applied to the anterior-superior iliac spines of the pelvis.

Still further in accordance with the embodiment of the present disclosure, creating the coordinate system comprises setting a cranial-caudal axis of the coordinate system of the pelvis as a cross-product of the anterior-posterior axis and of the medio-lateral axis.

Still further in accordance with the embodiment of the present disclosure, creating the coordinate system comprises obtaining a tilt of the pelvis relative to the medio-lateral axis relative and to a cranial-caudal axis from an instrument supporting the inertial sensor unit applied to the pelvis, and further comprises aligning the antero-posterior axis and the medio-lateral axis with said tilt.

Still further in accordance with the embodiment of the present disclosure, obtaining the frontal tilt of the pelvis comprises obtaining the tilt from the instrument applied to at least one of the anterior-superior iliac spines of the pelvis and to a pubic tubercle.

Still further in accordance with the embodiment of the present disclosure, creating the coordinate system comprises obtaining a lateral tilt of the pelvis relative to a cranial-caudal axis of the coordinate system from an instrument supporting the inertial sensor unit applied to the pelvis, and further comprises aligning the medio-lateral axis with said lateral tilt.

Still further in accordance with the embodiment of the present disclosure, obtaining the lateral tilt of the pelvis relative to the medio-lateral axis comprises obtaining the lateral tilt from the instrument applied to the anterior-superior iliac spines of the pelvis.

Still further in accordance with the embodiment of the present disclosure, the inertial sensor unit used in creating the coordinate system and the inertial sensor unit connected to the at least one surgical instrument is the same.

Still further in accordance with the embodiment of the present disclosure, the coordinate system of the pelvis is updated after setting the orientation of the at least one instrument.

Still further in accordance with the embodiment of the present disclosure, an orientation of the instrument is reset by obtaining readings from any one of the inertial sensor unit secured to the pelvis.

Still further in accordance with the embodiment of the present disclosure, resetting an orientation of the at least one instrument in the coordinate system comprises obtaining readings from the inertial sensor unit on the surgical instrument with the surgical instrument being oriented in a known orientation relative to the pelvis.

Still further in accordance with the embodiment of the present disclosure, obtaining readings from the inertial sensor unit in the known orientation comprises obtaining readings from the inertial sensor unit when a planar light source on the instrument points to landmarks on the pelvis.

In accordance with another embodiment of the present disclosure, there is provided a computer-assisted surgery system comprising: at least one calibrating instrument adapted to be applied to a pelvis in a known manner; at least one surgical instrument; a computer-assisted processor unit operating a surgical assistance procedure and comprising: at least one portable inertial sensor unit configured to be connected to the at least one calibrating instrument and the at least one surgical instrument, the portable inertial sensor unit outputting readings representative of its orientation; a geometrical relation data module providing a geometrical relation data between the orientation of the portable inertial sensor unit, of the at least one calibrating instrument and of the at least one surgical instrument; a coordinate system module for setting a coordinate system of the pelvis in which an anterior-posterior axis of the pelvis is generally in a direction of gravity, and in which a medio-lateral axis of the pelvis is obtained from readings of the at least one portable inertial sensor unit on the at least one calibrating instrument using the geometrical relation data therebetween; a tracking module for tracking movements of the at least one surgical instrument relative to the coordinate system using readings from the inertial sensor unit on the surgical instrument using the geometrical relation data therebetween, and calculating navigation data for the movements, the navigation data relating the orientation of the surgical instrument to the orientation of the pelvis; and an interface for outputting the navigation data.

Further in accordance with the other embodiment of the present disclosure, the at least one calibrating instrument is a medio-lateral digitizer adapted to contact anterior-superior iliac spines of the pelvis, and further wherein the coordinate system module obtains a lateral tilt of the pelvis relative to a cranial-caudal axis of the coordinate system from the medio-lateral digitizer and aligns the medio-lateral axis with said lateral tilt.

Still further in accordance with the other embodiment of the present disclosure, the at least one calibrating instrument is adapted to contact anterior-superior iliac spines and a pubic tubercle of the pelvis, and further wherein the coordinate system module obtains a tilt of the pelvis relative to a cranial-caudal axis and to the medio-lateral axis of the coordinate system, and aligns the antero-posterior axis and the medio-lateral axis with said lateral tilt.

Still further in accordance with the other embodiment of the present disclosure, the surgical instrument is one of an impactor and an acetabulum reamer.

Still further in accordance with the other embodiment of the present disclosure, the geometrical relation data module, the coordinate system module and the tracking module are integrated in the at least one portable inertial sensor unit.

Still further in accordance with the other embodiment of the present disclosure, a stand-alone processing device with an interface communicates with the at least one portable inertial sensor unit, the stand-alone processing device concurrently operating the surgical assistance procedure to provide guidance to a user.

Still further in accordance with the other embodiment of the present disclosure, an updated orientation module has a known orientation of the inertial sensor unit relative to the pelvis, and wherein the coordinate system module updates an orientation of the surgical instrument in the coordinate system using readings of the at least one portable inertial sensor unit when in said known orientation.

Still further in accordance with the other embodiment of the present disclosure, a support structure is adapted to be secured to the pelvis and having a mount for the portable inertial sensor unit, said known orientation comprising the portable inertial sensor unit in the support structure.

Still further in accordance with the other embodiment of the present disclosure, the at least one surgical instrument has a light source thereon emitting a planar beam, the known orientation comprising the at least one surgical instrument projecting the planar beam on predetermined landmarks of the pelvis.

DETAILED DESCRIPTION

Figure 2:
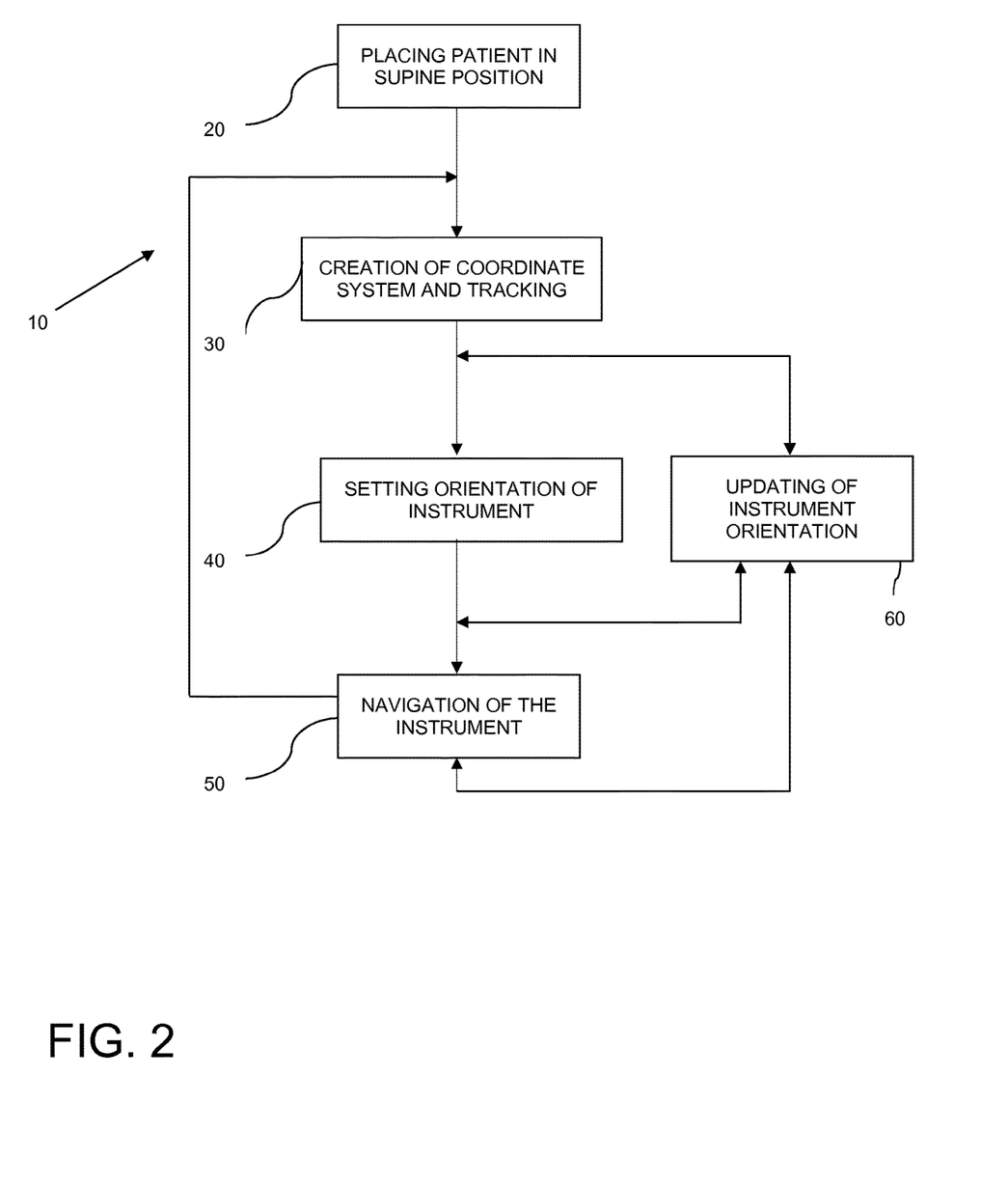
FIG. 2 is a flow chart of a method for navigating an instrument in computer-assisted hip surgery in accordance with the present disclosure.

Referring to the drawings and more particularly to FIG. 2, a method for navigating an instrument in computer-assisted hip surgery is generally shown at 10. The purpose of method 10 is to accurately navigate surgical instruments used in hip arthroplasty or like procedures, such as an acetabular reamer, a cup impactor, an impactor guiding pin, using inertial sensors. By navigating instruments, the present disclosure refers to the process of providing orientation data relating an instrument to a bone, to guide an operator in performing surgical maneuvers of the instrument relative to the bone.

Figure 1A:
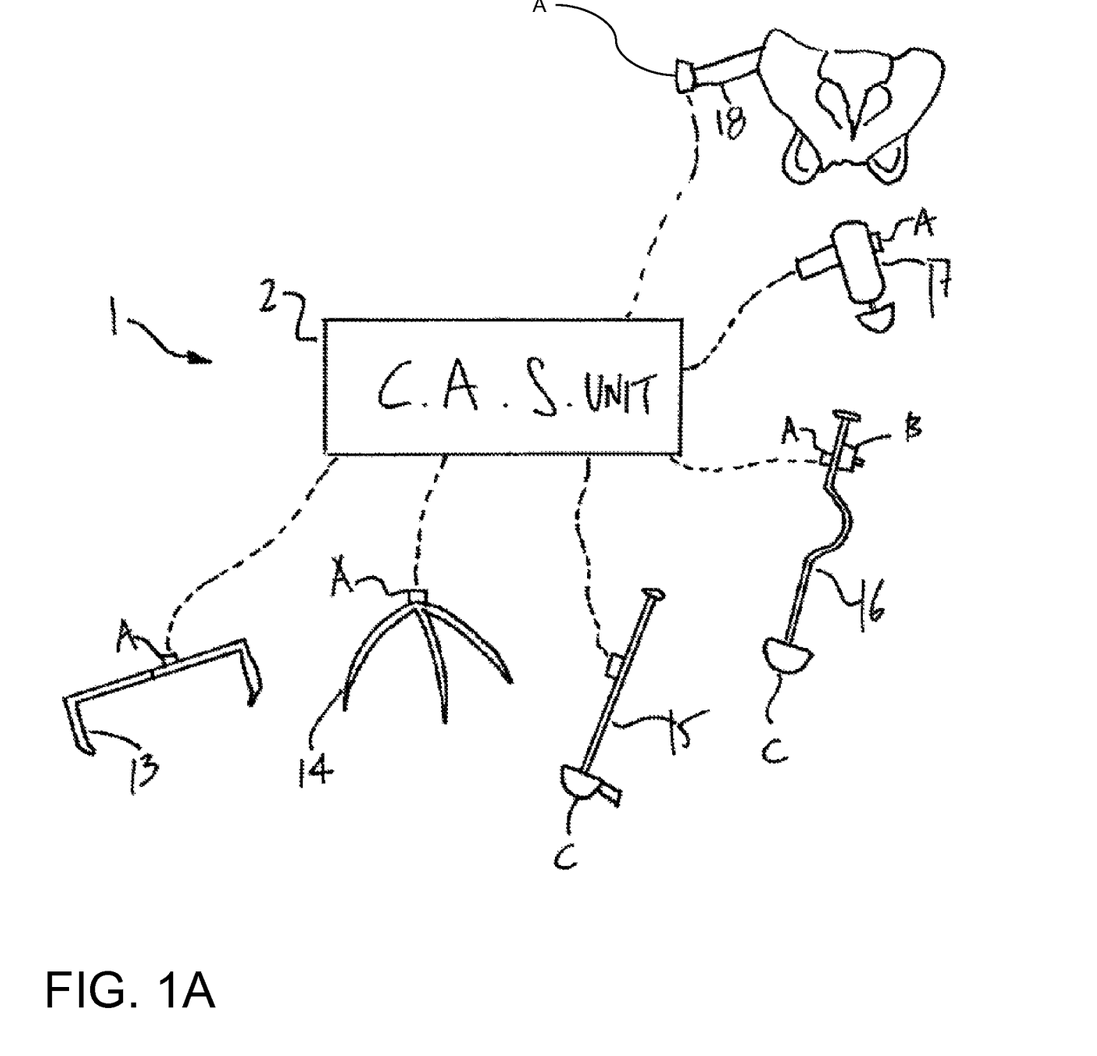
FIG. 1A is a schematic view of a system for navigating instruments in computer-assisted hip surgery.

Referring to FIG. 1A, a system for navigating instruments in computer-assisted hip surgery is generally shown at 1, and is of the type used to implement the method 10, as will be detailed below. The system 1 comprises a computer-assisted surgery (CAS) processing unit 2, shown as a stand-alone unit in FIG. 1. It is however pointed out that the CAS processing unit 2 may be integrated into one or more inertial sensor units A, also known as pods that are mounted to the various devices and instruments of the system 10, or as a module of a computer or portable device, among other possibilities.

Figure 1B:
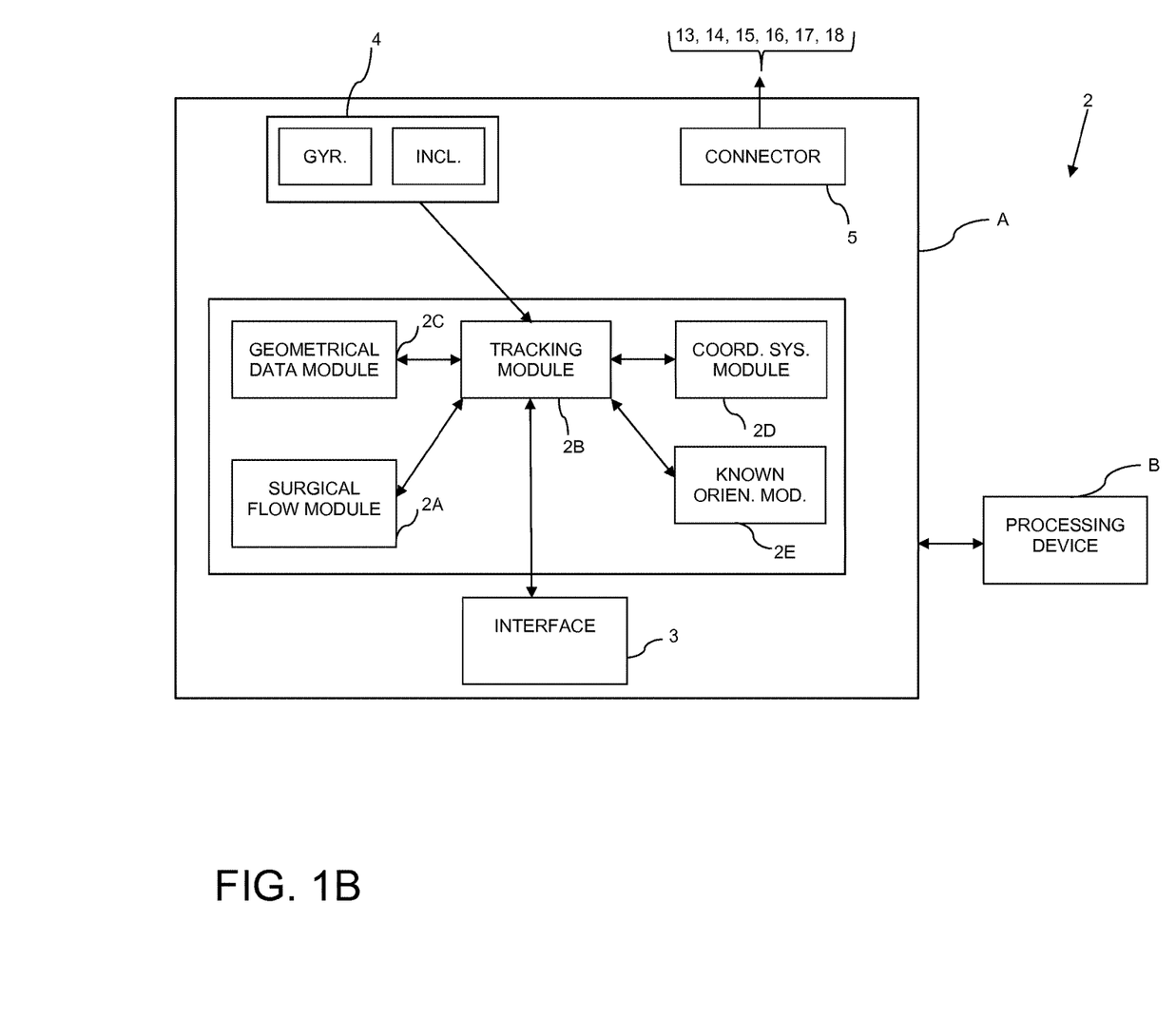
FIG. 1B is a schematic view of an inertial sensor unit of the system of FIG. 1A.

For instance, one of the inertial sensor units A is shown in FIG. 1B. The system 1 may have one or more of the inertial sensor units A, with a single one being shown in FIG. 1B for clarity. The inertial sensor unit A incorporates the processing unit 2 and may thus be equipped with a user interface(s) 3 to provide the navigation data, whether it be in the form of LED displays, screens, numerical displays, etc. Alternatively, the inertial sensor unit A may be connected to a stand-alone processing device B that would include a screen or like monitor, to provide additional display capacity and surface. By way of example, the processing device B is a wireless portable device such as a tablet in a wired or wireless communication with the inertial sensor unit A.

The inertial sensor unit A may be known as micro-electro-mechanical sensors (MEMS) and may include one or more of inertial sensors 4, such as accelerometers, gyroscopes, inclinometers, magnetometers, among other possible inertial sensors. The inertial sensors 4 are sourceless sensors automatically providing data influenced by natural phenomena, such as gravity. The inertial sensor unit A also have a body, typically defined by a casing, giving the inertial sensor unit A a connector 5, by which the inertial sensor unit A may be secured to instruments and tools as described hereinafter.

The processing unit 2 comprises different modules to perform the navigation. A surgical flow module 2A may be used in conjunction with the user interface 3 or a processing device B to guide the operator through the steps leading to the navigation, e.g., the steps of method 10. This may entail providing a step-by-step guidance to the operator, and prompting the operator to perform actions, for instance pressing on a "record" interface that is part of the interface 3, for the system 1 to record instant orientations. While this occurs throughout the surgical procedure, the prompting and interactions between the system 1 and the user will not be described in a remainder of the description, as they will implicitly occur. It is contemplated to have the surgical flow module 2A present in the processing device B, with concurrent action between the inertial sensor unit A and the processing device B to guide the operator to navigation and surgery, and with a communication with the operator to record the progress of the procedure.

A tracking module 2B may also be part of the processing unit 2. The tracking module 2B receives readings from the inertial sensors 4, and converts these readings to useful information, i.e., the navigation data. As described above, the navigation data may be orientation data relating an instrument to the pelvis. In order to output the navigation data via the user interface 3 or processing device B, the processing unit 2 may be preprogrammed with geometrical relation data module 2C. The geometrical relation data module 2C is the three-dimensional relation between the inertial sensor unit A via its connector 5 and instruments and tools. The inertial sensor unit A is designed such that its connector 5 may be connected in a single possible orientation to the instruments and tools, such that the orientation of the inertial sensor unit A is known relative to the instruments and tools to which it is connected when turned on. By way of the connector 5 and the geometrical relation data module 2C, the inertial sensor units A may be portable and detachable units, used with one device/instrument, and then transferred to another device/instrument, preserving in the process orientation data of the global coordinate system.

The coordinate system module 2D creates the coordinate system during the steps of method 10 leading to navigation, and may subsequently be updated. The coordinate system 2D is the virtual frame by which the orientation of the instruments and tools is related to the orientation of the bone.

The known orientation module 2E is used in an updating of the coordinate system, and represents a known orientation between the inertial sensor unit A and the pelvis, by which the system 1 may update the coordinate system.

Referring to FIG. 1A, calibrating instruments or devices that may be used with the system 1 include non-exhaustively a medio-lateral digitizer 13, a three-pronged registration device 14, an acetabular rim digitizer 15, all of which are used to define the coordinate system for the pelvis, a.k.a. world coordinate system, global coordinate system, pelvic frame of reference, etc, for subsequent navigation. Surgical instruments that may subsequently be used with the system 1 include non-exhaustively a cup impactor 16, an acetabular reamer 17, an impactor guiding pin, a support structure 18, etc. The geometrical relation data module 2C is programmed in to the inertial sensor unit A for specific use with the devices and instruments described above. Accordingly, when an inertial sensor unit A is mounted to one of the devices and instruments, the relation between the device/instrument and a coordinate system of the inertial sensor unit A is known (in contrast to a global coordinate system) and part of the geometrical relation data module 2C. For example, the relation may be between an axis or a 3D coordinate system of the device/instrument and the coordinate system of the inertial sensor unit A.

The navigation of instruments is intended to mean tracking at least some of the degrees of freedom of orientation in real-time or quasi-real time, such that the operator is provided with navigation data calculated by computer assistance, which navigation data is representative of hip surgery parameters, such as anteversion and inclination, among other examples. The inertial sensors A used in the following method may be interrelated in the global coordinate system (hereinafter, coordinate system), provided appropriate steps are taken to record or calibrate the orientation of the inertial sensors A in the coordinate system. The coordinate system serves as a reference to quantify the relative orientation of the different items of the surgery, i.e., the instruments and devices relative to the pelvis.

The method 10 generally comprises different subprocedures. According to 10, the patient is placed in a supine position (lying on his/her back) on the table plane, and the subsequent subprocedures will be based on the orientation of the patient in the supine position, as the supine position will influence the subprocedures. According to 30, the pelvic coordinate system is created. According to 40, the navigated instrument is initialized. According to 50, the instrument is navigated. According to 60, the orientation of the navigated instrument in the pelvic coordinate system is updated. Other subprocedures to method 10 may be added in any appropriate sequence. For instance, while not part of the steps of the method described herein, resection of the femur may be performed to expose the acetabulum.

Creation of the Coordinate System 30 and Tracking

In order to create the coordinate system 30, i.e., register the pelvic orientation as (also known as pelvic tilt), the orientation of the pelvis must be determined relative to the coordinate system. When the patient lies in a supine position, i.e., lying on his/her back, the coordinate system may be defined as follows:

A first axis, referred to as a Z axis, is generally aligned with gravity (i.e., normal to a ground plane), and representative of an anterior-posterior direction. As seen hereinafter, the orientation of the Z axis may be adjusted as influenced by a pelvic tilt;

A second axis, referred to as an X axis is aligned with the medio-lateral axis of the patient projected on the table plane, the table plane matching the ground plane. The medio-lateral axis extends in a lateral direction, e.g., from one anterior-superior iliac spine (ASIS) to another; and A third axis, referred to as a Y axis, is the cross-product between the Z axis and the X axis, and is representative of a cranial-caudal direction.

The above axes are one among numerous possibilities. For example, it may be the X axis that is aligned with gravity, the X, Y and Z nomenclature being used as convention for the present case. As another example, the X axis may be the medio-lateral axis of the patient, i.e., not a projection thereof on the table plane, etc. Stated differently, the definition of the coordinate system may be arbitrary, and may hence have any appropriate definition other than the ones described above. However, the above-referred definition is practical in that the axes are aligned with known landmarks, such as gravity and the table plane.

According to an embodiment, in order to register the pelvic orientation 30, the patient radiographical plane is defined as being aligned with the table plane. Hence, the pelvis of the patient lying in supine position is assumed to be without lateral tilt (i.e., about the Y axis) or anterior-posterior tilt (i.e., about the X axis). In such an embodiment, navigation angles (e.g., inclination) will be measured with reference to the medio-lateral axis projected on the table plane during navigation 50, as the table plane is deemed to be parallel to the frontal plane of the patient.

Alternatively, in accordance with other embodiments, no assumptions may be made regarding the pelvic tilt, whereby maneuvers must be made to proceed with the registration of the pelvic orientation 30. For example, according to an embodiment, registration is performed using the three-pronged registration device 14 (FIG. 1A) equipped with an inclinometer positioned at a fixed orientation relative to the plane formed by the three prongs. The prongs could be positioned on three landmarks defining a patient frontal plane (i.e., contra-lateral ASIS, lateral ASIS and pubic tubercle). The three-pronged registration device 14 would be used to measure both the lateral tilt of the pelvis and the anterior/posterior tilt of the pelvis. The pelvic tilt data measured by the inclinometer would be recorded by the inertial sensor unit A using the geometrical relation data module 2C knowing the relation between the inertial sensor unit A and the three-pronged registration device 14, and recorded as part of the coordinate system in the coordinate system module 2D. In recording the pelvic tilt, the system 1 may orient the medio-lateral axis and/or cranial-caudal axis to match the measured pelvic tilt.

In another embodiment, a device such as an acetabulum rim digitizer 15 (FIG. 1A) may be used to determine the current inclination of the pelvis. The acetabulum rim digitizer 15 may be used with pre-operative imagery to evaluate rim orientation relative to pelvic orientation. The acetabulum rim digitizer 15 may include a patient-specific surface, machined to be a negative of a bone surface for high accuracy complementary engagement. An exemplary rim digitizer 15 is as shown in U.S. Patent Application Publication No. 2014/0031722, incorporated herein by reference.

In yet another embodiment, a medio-lateral digitizer 13 may be used with an inertial sensor unit A secured thereon, based on the assumption that the cranial-caudal axis (i.e., longitudinal axis) of the patient in supine position is parallel to the ground plane (i.e., no antero-posterior tilt of the patient frontal plane with regards to the radiographical plane, or table plane). The medio-lateral digitizer 13 may be as described in U.S. Patent Application Publication No. 2014/0031829, incorporated herein by reference, and is thus used to measure the lateral tilt of the pelvis. The medio-lateral digitizer 13 may be adjustable in size to have its ends contact two landmarks of the pelvis. For example, the medio-lateral digitizer 13 may contact the two ASIS to determine an orientation of the medio-lateral axis relative to the table plane, and hence provide sufficient data for the global coordinate system to be complete. The pelvic tilt data measured by the inertial sensor unit A on the medio-lateral digitizer 13 would be recorded using the geometrical relation data module 2C knowing the relation between the inertial sensor unit A and medio-lateral digitizer 13, and recorded as part of the coordinate system of the coordinate system module 2D. In recording the pelvic tilt, the system 1 may orient the medio-lateral axis to match the measured pelvic tilt, i.e. aligns the medio-lateral axis with the pelvic tilt. It is observed that an orientation of the antero-posterior axis may be adjusted or corrected as well by the realignment of the medio-lateral axis, whereby the antero-posterior axis is generally aligned with gravity as general pointing in the same direction, although not parallel to one another.

The pelvic tilt data measured by the inertial sensor unit A of the medio-lateral digitizer 3 would then be part of the coordinate system as set by the coordinate system module 2D, and taken into consideration when initializing the instruments in 40 for subsequent navigation in 50.

As a result of the creating of the coordinate system with the coordinate system module 2D, the orientation of the pelvis is used as a reference by the tracking module 2B of the inertial sensor unit A. According to an embodiment, the tracking module performs dead reckoning to maintain its reference to the coordinate system of the pelvis, using gyroscope readings from the inertial sensors 4. Dead reckoning implies the integration of all the angular velocity data through time to evaluate the rotation of the inertial sensor unit A, thus allowing the tracking of its orientation in space.

It may be necessary to repeat step 30 in the event that the pelvis moves. For example, some of the steps described hereinafter, and other steps such as impacting a cup C, may result in the movement of the pelvis on the table. The system may hence prompt the user to repeat the step 30.

Setting Instrument Orientation 40

According to the setting 40 of the orientation of the navigated instrument, the orientation of any of the instruments 16, 17, etc is set (i.e., recorded) in the global coordinate system, so as to subsequently track the instruments relative to the pelvis. Stated differently, the instruments must be initialized (i.e., calibrated) for their orientation in the global coordinate system to be known. The instruments may be one or more of an acetabular reamer 16, a cup impactor 17, an impactor guiding pin, cup validation device, etc used in surgery.

In an embodiment, the inertial sensor unit A used for the creating of the coordinate system 30 (e.g., that was on the medio-lateral digitizer 13 or three-pronged registration device 14 shown in FIG. 1A) can be detached therefrom after the registration 30 is completed while being tracked by the tracking module 2B, and then be fixated onto the navigated instrument (e.g., instruments 16 or 17) to preserve the global coordinate system, using the geometrical relation data module 2C between the connector 5 and an instrument axis as programmed in the inertial sensor unit A. As mentioned above, the inertial sensors 4 of the inertial sensor unit A continuously track the orientation of the inertial sensor unit A while being fixated on the navigated instrument. As a result, the coordinate system now comprises an orientation of the instrument relative to the pelvis.

It is contemplated to use more than one inertial sensor unit A, for instance performing a transfer of data between inertial sensor units A using the same principle of known geometrical data for setting orientations in the coordinate system. The use of more than one inertial sensor unit A may allow a concurrent tracking of a bone and of an instrument.

Navigation of Instrument 50

The setting 40 enables the determination of the three-axis orientation of the instrument 6, 7 by the CAS processing unit 2 in the global coordinate system. The setting 40 entails recording an orientation of the instruments using the geometrical relation data module 2C to provide the geometrical relation data between the instrument and the inertial sensor unit A. The tracking module 2A may thus track the orientation of the instruments in the coordinate system provided by the coordinate system module 2D. The CAS processing unit 2 may track orientation changes of the instrument 16, 17 in the global coordinate system. i.e., relative to the pelvis, using the readings of the inertial sensor unit A. The CAS processing unit 2 may for example provide inclination or anteversion data in real-time or quasi-real-time. Essentially, the data may be regarded as the anticipated inclination and/or anteversion of the acetabular cup C if the tool alters the acetabulum in a given manner in the case of a reamer 17, or based on current orientation of the impactor 16 relative to the pelvis. The navigation data may be in an appropriate format, such as numerical values, models of the bone and instrument, or visual indications that desired or planned relative orientations between instruments and bone are reached.

As mentioned previously, the navigated instrument may be an impactor 16, by which the acetabular cup C may be properly oriented prior to impaction. In another embodiment, the navigated instrument is an instrument used to secure an impactor guiding pin to the pelvis in a desired orientation, which pin can be used to guide the impactor even beyond the impaction. In yet another embodiment, the navigated instrument is a validation surface that can be positioned flat onto the acetabular cup C once impacted in order to validate the orientation of the acetabular cup C.

Updating Orientation of the Instrument in the Coordinate System 60

Over time, the tracking performed by the tracking module 2B of the inertial sensor unit A may lose precision. For example, dead reckoning operations may become less accurate during the procedure, considering that dead reckoning involves integration of the angular velocity data over time. Accordingly, at any point after the creating 30 of the coordinate system, the CAS processing unit 2 may prompt the operator to update (a.k.a., reset, reinitialize) the orientation of the navigated instrument in the coordinate system. Different subprocedures or steps may be employed to update the coordinate system.

In an embodiment, the inertial sensor unit A has both a gyroscope and an inclinometer as inertial sensors 4. The inclinometer provides data related to two degrees of freedom (DOF) with regards to the orientation of the navigated instrument in the global coordinate system. A maneuvering method is then required to update the orientation of the instrument in the coordinate system in a missing axis of orientation, referred to as yaw, i.e., to update the tracking, such that by this maneuvering method, readings may be obtained from the inertial sensor unit A on the instrument with the instrument being oriented in a known orientation relative to the pelvis, in a known orientation module 2E.

One method considered to fix the yaw, i.e., reach the known orientation, is to use a planar light pod B as in FIG. 1A (i.e., a laser or light source which projects a line onto a surface) mounted to the navigated instrument 16 in a known orientation programmed in the known orientation module 2E, the instrument 16 having a cup-shaped end or cup implant C to be received in the acetabulum. By orienting the instrument 16 such that the planar light pod B points the laser line onto both ASIS, the normal of the laser plane can be defined as being aligned with the Y axis of the coordinate system. Using this information, and knowing the orientation of the laser pod B with respect to the inertial sensor unit A and navigated instrument axis as programmed as geometrical relation data module 2C in the CAS processing unit 2 (FIG. 1), the third rotational DOF is calculable by the known orientation module 2E, and the orientation of the instrument in the global coordinate system may be updated or reset in the coordinate system module 2D.

In yet another embodiment, the navigated instrument is the acetabulum reamer 17, allowing the operator to orient the reaming device to ream according to plan.

In accordance with an alternative method, a support structure 18 (FIG. 1A) is used to update the coordinate system by being fixed to the pelvis. The workflow would be as follows:

1 prior to dislocation, the support structure 18 is pinned or secured to the pelvis, for example to the iliac crest, the support structure 18 being of the type configured to receive an inertial sensor unit A thereon;
2 the pelvic lateral tilt is registered using the medio-lateral digitizer 13 (FIG. 1A) or any other calibrating tool with an inertial sensor unit A thereon, in the manner described above, and the coordinate system is created;
3 the inertial sensor unit A is then detached from the medio-lateral digitizer 13 and then attached to the support structure 18. Tracking is performed during the transfer to preserve the orientation of the inertial sensor unit A in the global coordinate system, and the orientation of the inertial sensor unit A in the support structure 18 is recorded as a known orientation by the known orientation module 2E;
4 the femoral head is then resected to allow access to the acetabulum, other operations are performed, etc;
5 when updating 60 is necessary, the inertial sensor unit A is attached to the support structure 18, and the inertial sensor unit A retrieves the known orientation between the pelvis and inertial sensor unit A in the support structure 18, to reset the coordinate system with the coordinate system module 2E;
6 the inertial sensor unit A may then be connected to any surgical instrument for subsequent navigating.

While the methods and systems described herein have been described and shown with reference to particular steps performed in a particular order, it will be understood that these steps may be combined, subdivided or reordered to form an equivalent method without departing from the teachings of the present invention. Accordingly, the order and grouping of the steps is not a limitation of the present invention. The method 10 may be performed on bone models or cadavers as well.

The invention claimed is:

1. A method for navigating a surgical instrument relative to a pelvis in computer-assisted hip surgery with a patient in a supine position on a table plane, comprising:
creating a coordinate system for a pelvis with at least one an inertial sensor unit, the coordinate system using a direction of gravity for setting an anterior-posterior axis of the pelvis, and comprising a medio-lateral axis of the pelvis;
obtaining a tilt of the pelvis relative to the medio-lateral axis and/or to a cranial-caudal axis, the tilt including a plane representative of an orientation of the pelvis;
tracking the at least one inertial sensor unit in the coordinate system of the pelvis;
setting an orientation of at least one surgical instrument with the at least one inertial sensor unit thereon by determining three rotational degrees of freedom of the instrument in the coordinate system of the pelvis;
tracking movements of the at least one surgical instrument relative to the coordinate system using readings from the at least one inertial sensor unit on the surgical instrument; and
outputting navigation data for the movements, the navigation data relating the orientation of the surgical instrument to the orientation of the pelvis.

2. The method according to claim 1, wherein outputting navigation data comprises outputting anteversion and/or inclination angles of the surgical instrument relative to the pelvis.

3. The method according to claim 1, wherein creating the coordinate system for the pelvis comprises obtaining the medio-lateral axis from an instrument supporting the inertial sensor unit applied to the anterior-superior iliac spines of the pelvis.

4. The method according to claim 1, further comprising aligning the anterior-posterior axis with said tilt.

5. The method according to claim 4, wherein obtaining the tilt of the pelvis comprises obtaining the tilt from the at least one surgical instrument applied to at least one of the anterior-superior iliac spines of the pelvis and to a pubic tubercle.

6. The method according to claim 1, wherein the inertial sensor unit used in creating the coordinate system and the inertial sensor unit connected to the at least one surgical instrument is the same.

7. The method according to claim 1, further comprising resetting an orientation of the at least one instrument in the coordinate system of the pelvis after setting the orientation of the at least one instrument.

8. The method according to claim 7, wherein resetting an orientation of the at least one instrument in the coordinate system comprises obtaining readings from any one of the inertial sensor unit secured to the pelvis.

9. The method according to claim 7, wherein resetting an orientation of the at least one instrument in the coordinate system comprises obtaining readings from the inertial sensor unit on the surgical instrument with the surgical instrument being oriented in a known orientation relative to the pelvis.

10. The method according to claim 9, wherein obtaining readings from the inertial sensor unit in the known orientation comprises obtaining readings from the inertial sensor unit when a planar light source on the instrument points to landmarks on the pelvis.

11. The method according to claim 1, further comprising prompting an operator to perform actions by an interface.

* * * * *